(12) United States Patent
Karazivan

(10) Patent No.: US 8,992,216 B2
(45) Date of Patent: Mar. 31, 2015

(54) INTERPROXIMAL TOOTH DEFECTS DETECTION

(75) Inventor: Naim Karazivan, Repentigny (CA)

(73) Assignee: Dentsply Canada Ltd., Woodbridge, ON (CA)

( * ) Notice: Subject to any disclaimer, the term of this patent is extended or adjusted under 35 U.S.C. 154(b) by 919 days.

(21) Appl. No.: 12/065,093

(22) PCT Filed: Aug. 29, 2006

(86) PCT No.: PCT/CA2006/001422
§ 371 (c)(1),
(2), (4) Date: Feb. 28, 2008

(87) PCT Pub. No.: WO2007/025377
PCT Pub. Date: Mar. 8, 2007

(65) Prior Publication Data
US 2008/0248447 A1    Oct. 9, 2008

(30) Foreign Application Priority Data
Aug. 29, 2005   (CA) ..................... 2517252

(51) Int. Cl.
*A61C 3/00*      (2006.01)
*A61B 5/00*      (2006.01)

(52) U.S. Cl.
CPC .................. *A61B 5/0088* (2013.01)
USPC ........... 433/29; 433/215; 356/243.8; 600/477

(58) Field of Classification Search
USPC ........... 433/215, 29, 31; 382/128; 606/15–17; 356/243.8, 477, 479, 481; 600/477; 362/572–573, 804; 607/88–95
See application file for complete search history.

(56) References Cited

U.S. PATENT DOCUMENTS

| | | | | |
|---|---|---|---|---|
| 4,184,175 | A * | 1/1980 | Mullane, Jr. .................... | 348/66 |
| 4,479,499 | A * | 10/1984 | Alfano .......................... | 600/477 |
| 4,515,476 | A * | 5/1985 | Ingmar ......................... | 356/318 |
| 5,306,144 | A * | 4/1994 | Hibst et al. .................... | 433/29 |
| 6,053,731 | A * | 4/2000 | Heckenberger ................ | 433/29 |
| 6,135,774 | A * | 10/2000 | Hack et al. ..................... | 433/215 |
| 6,179,611 | B1 * | 1/2001 | Everett et al. .................. | 433/29 |
| 6,186,780 | B1 * | 2/2001 | Hibst et al. .................... | 433/29 |
| 6,201,880 | B1 * | 3/2001 | Elbaum et al. ................. | 382/100 |
| 6,406,293 | B1 * | 6/2002 | Burstein ......................... | 433/29 |

(Continued)

FOREIGN PATENT DOCUMENTS

| WO | 2005013843 A1 | 2/2005 |
|---|---|---|
| WO | WO 2005/013843 A2 * | 2/2005 |
| WO | 2007009234 A1 | 1/2007 |

OTHER PUBLICATIONS

Examination Report of the European Patent Application, Communication pursuant to Article 94(3) EPC, Dated: Feb. 2, 2011.

(Continued)

*Primary Examiner* — Cris L Rodriguez
*Assistant Examiner* — Hao D Mai
(74) *Attorney, Agent, or Firm* — Anglehart et al.

(57) ABSTRACT

There is provided a method for detecting interproximal tooth defects such as caries by injecting light at one or more wavelengths into a tooth and detecting reflected/diffracted light or emitted fluorescence. The detected light intensity is characteristic of a healthy or diseased tooth in the interproximal area.

10 Claims, 5 Drawing Sheets

(56) References Cited

U.S. PATENT DOCUMENTS

| | | | | |
|---|---|---|---|---|
| 6,580,935 | B1* | 6/2003 | Wach et al. | 600/310 |
| 6,584,341 | B1* | 6/2003 | Mandelis et al. | 600/476 |
| 6,997,883 | B1* | 2/2006 | Hahn | 600/560 |
| 7,270,543 | B2* | 9/2007 | Stookey et al. | 433/215 |
| 7,577,284 | B2* | 8/2009 | Wong et al. | 382/128 |
| 2002/0093655 | A1* | 7/2002 | Everett et al. | 356/369 |
| 2002/0107448 | A1* | 8/2002 | Gandjbakhche et al. | 600/476 |
| 2003/0170586 | A1* | 9/2003 | Cozean et al. | 433/29 |
| 2004/0236232 | A1* | 11/2004 | Jonusauskas et al. | 600/477 |
| 2005/0003323 | A1* | 1/2005 | Katsuda et al. | 433/29 |
| 2005/0100866 | A1* | 5/2005 | Arnone et al. | 433/215 |
| 2005/0181333 | A1* | 8/2005 | Karazivan et al. | 433/215 |
| 2005/0283058 | A1 | 12/2005 | Choo-Smith et al. | |
| 2006/0223032 | A1* | 10/2006 | Fried et al. | 433/215 |
| 2007/0021670 | A1* | 1/2007 | Mandelis et al. | 600/473 |
| 2007/0134615 | A1* | 6/2007 | Lovely | 433/29 |
| 2007/0248931 | A1* | 10/2007 | Wong et al. | 433/29 |
| 2008/0118886 | A1* | 5/2008 | Liang et al. | 433/29 |
| 2009/0087811 | A1* | 4/2009 | Ertl | 433/29 |
| 2011/0085715 | A1* | 4/2011 | Yan et al. | 382/128 |

OTHER PUBLICATIONS

International Preliminary Report on Patentability for International Application No. PCT/CA2006/001422.
Response as filed following communication pursuant to rules 70(2) and 70a(2) EPC, Concerning European Patent Applicaiton, dated: Nov. 18, 2010.
Written Opinion for International Application No. PCT/CA2006/001422, Dec. 1, 2006.
Journal of Biomedical Optics 10(3), May/Jun. 2005, "Ex Vivo detection and characterization of early dental caries by optical coherence tomography and Raman spectroscopy" A. C.-T . Ko , Lin-P'ing Choo-Smith , M. Hewko, L. Leonardi, and M. G. Sowa, C. C. S. Dong , P. Williams , B. Cleghorn, pp. 031118-1-031118-2 , XP040213741.
Patara Ngaotheppitak , Cynthia L. Darling, Daniel Fried : "PS-OCT of natural pigmented and nonpigmented interproximal caries lesions" Proc . SPIE, vol. 5687, Mar. 31, 2005, pp. 25-33 , XP040199108.
Raymond J . Jeon , Andreas Mandelis, Victor Sanchez, and Stephen H. Abrams : "Nonintrusive, noncontacting frequency-domain photothermal radiometry and luminescence depth profilometry of carious and artificial subsurface lesions in human teeth" Journal of Biomedical Optics, Jul. 12, 2004 pp. 804-819, XP040194535.
Ngaotheppitak Patara et al : "PS-OCT of occlusal and interproximal caries lesions viewed from occlusal surfaces" Progress in Biomedical Optics and Imaging, vol. 7, No. 23, Feb. 15, 2006 pp. 61370L-61370I , XP009132147.
Daniel Fried et al: "Imaging caries lesions and lesion progression with polarization sensitive optical coherence tomography" Journal of Biomedical Optics, SPIE, vol. 7, No. 4, Oct. 1, 2002 pp. 618-627, XP009128471.
J .W. Van De Rijke , N. pas, J.J . Ten Bosch: "Model Study for Quantification of Approximal Caries with a Fluorescent Dye" Caries Res, vol. 24, No. 6, 1990 , pp. 436-440, XP009132188.
The International Search Report, PCT/CA2006/001422 Apr. 15, 2010.
European Search Report, PCT/CA2006/001422 Jan. 24, 2008.
Canadian appl 2621782 first Office Action dated Jun. 3, 2013, with related claims.
Canadian appl 2621782 Second Office Action dated May 2, 2014, with related claims.

* cited by examiner

INTERPROXIMAL TOOTH DEFECTS DETECTION

CROSS-REFERENCE TO RELATED APPLICATION

This application claims priority on Canadian patent application No. 2,517,252 filed Aug. 29, 2005 and entitled "DETECTION DE LA CARIE INTERPROXIMALE A L'AIDE D'UNE SONDE OPTIQUE EXAMINANT LA SURFACE OCCLUSALE DE LA DENT".

FIELD OF THE INVENTION

The invention relates to the optical detection of tooth defects and more specifically it relates to the optical detection of tooth defects in the interproximal area.

BACKGROUND OF THE INVENTION

There are various known methods that are used to detect the presence of dental caries, including visual and tactile investigations using the usual dental explorer. These methods and instruments have their limits and cannot detect dental caries reliably, especially when the dental caries is proximal and when the decay is at an initial stage. X-ray investigation of teeth structure is also not reliable for detecting dental caries at the beginning of their formation in regions where a too great superimposition of enamel is present on the X-ray film. These obstructing superimpositions of teeth structures are more typical for the occlusal aspect of the teeth, and when the angle between the teeth alignment and the X-ray irradiation axis induces superimposition. The X-ray evaluation technique also exposes the patient to potentially harmful radiations.

Transillumination is another technique used to detect dental caries. By irradiating visible light toward a tooth from an aspect (e.g. lingual) and by observing via another aspect (e.g. buccal) the transmitted light, the operator can sometimes confirm the diagnosis of dental caries by observing a luminosity contrast induced by a dental caries. This technique is not suitable for all dental caries, especially for dental caries at their beginning phase. Furthermore the device used for transillumination detection of caries is large and not easy to manipulate in the mouth.

Other devices have been devised for the detection of dental caries using luminescence or fluorescence spectroscopy with variable efficiencies depending, amongst others, on the cleanliness of the tooth surface. When irradiated with one or more initial radiations at a specific wavelength, some tooth structures generate a second radiation with a wavelength that is different from the initial radiations. The intensity and wavelength of such a second radiation is different for sound tooth structures from those for decayed tooth structures. See U.S. Pat. No. RE31,815, U.S. Pat. No. 4,479,499, U.S. Pat. No. 6,186,780, U.S. Pat. No. 6,102,704, U.S. Pat. No. 6,053,731, U.S. Pat. No. 6,135,774 and U.S. Pat. No. 5,306,144, and German Patent Publications No. DE-30 31 249-C2, No. DE-42 00 741-A1, No. DE-U1-93 17 984, No. DE-303 1249-C2 and No. DE-19541686-A1. In most cases, these devices include a laser to generate the initial exciting radiation, which can be potentially harmful to the patient.

The above described optical approaches are however sometimes inadequate for the detection of interproximal caries. Different approaches have been suggested with a view to better detect interproximal caries. These approaches are mostly based on special probes that try to reach the interproximal area. The making and manipulation of such probes are complex and not convenient.

There is therefore a need for improved optical method for the detection of caries and in particular interproximal caries.

SUMMARY OF THE INVENTION

In a broad aspect of the invention there is provided a method for the optical detection of tooth defects in the interproximal region. The method advantageously enables to probe the interproximal region without having to reach the region with on optical probe.

Thus in one aspect of the invention there is provided a method for detection of an interproximal defect in a tooth, comprising injecting incident light at an injection point in a first tooth region at one or more wavelengths, such that said incident light can reach said interproximal defect substantially through enamel structure; detecting reflected/refracted or re-emitted light in a second tooth region; analyzing said detected light to provide a signal indicating a presence of said interproximal defect; and wherein said first and said second tooth regions are other than the interproximal region.

In an aspect of the invention said first and said second region are the occlusal surface of said tooth.

In another aspect the step of analyzing comprises obtaining an intensity of said detected light and comparing said intensity with reference intensities obtained from healthy interproximal tooth regions and regions exhibiting defects.

In yet another aspect the intensity is detected at two or more wavelengths to provide intensity coordinates in two or more dimensional space, and wherein said coordinates are compared to reference coordinates of healthy tooth regions and tooth regions exhibiting defects.

BRIEF DESCRIPTION OF THE DRAWINGS

Further features and advantages of the present invention will become apparent from the following detailed description, taken in combination with the appended drawings, in which.

DETAILED DESCRIPTION OF THE INVENTION

In the present description the term "defect" or "tooth defect" is used to refer to alterations in the tooth structure or physiology such as caries (demineralization), plaque, dental concretion (e.g.calculus), fracture in tooth structure, blood in gingival or bone, tartar and the like.

Figure 1:
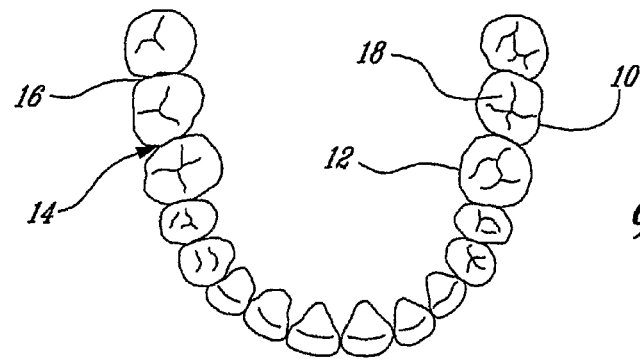
FIG. 1 is a schematic diagram of teeth arrangements in the mouth.
Figure 2:
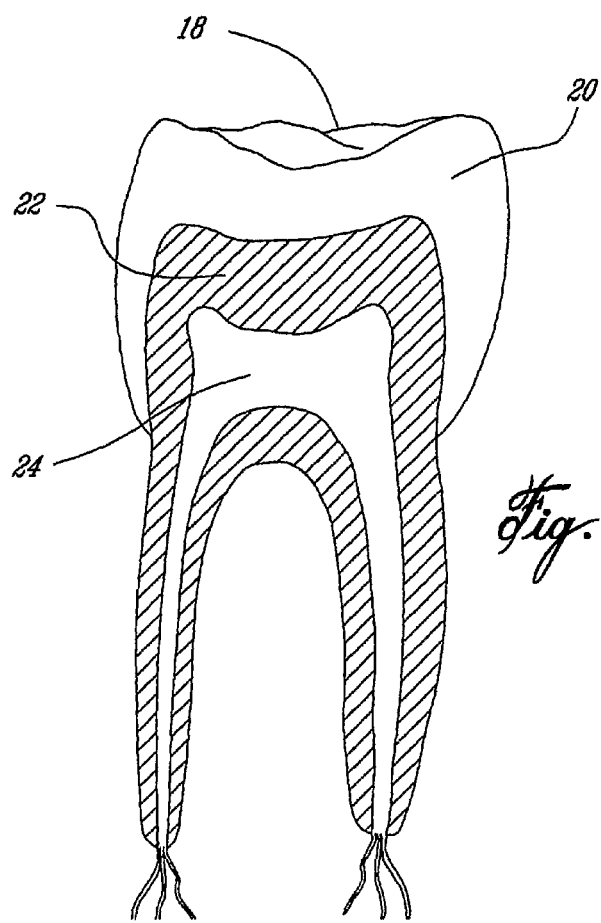
FIG. 2 is a cross-sectional view of a tooth revealing the internal structures.

A schematic representation of teeth with reference to their anatomy is shown in FIG. 1. The surfaces of the teeth comprise the facial 10, lingual 12, mesial 14 and distal 16 surfaces. The facial surface of a tooth faces the cheeks or lips. The lingual surface faces toward the tongue. There are two proximal surfaces: The mesial surface is the proximal surface closest to the front of the mouth and the distal surface is the proximal surface opposite the mesial surface (towards the back of the mouth). Between the mesial surface of one tooth and the distal surface of the next tooth is the interproximal space. The top of the tooth comprises the occlusal surface 18 (for the bicuspids and molars). A typical cross-sectional view of a tooth structure is shown FIG. 2 revealing the internal structure of the tooth. Shown in this figure is the enamel 20 which comprises the outer surface of the tooth, the dentin 22 which is a hard and porous tissue located under the enamel and the pulp 24 which comprises blood vessels and nerves.

The interproximal space and the mesial and distal surfaces are particularly difficult to inspect to assess the presence of defects such as caries. In the present invention it has been surprisingly found that light injected in a tooth can be used to detect interproximal tooth defects without having to position a light probe in the interproximal area. It is therefore shown in the present invention that optical detection of a defect such as a carie can be achieved using reflection/refraction or luminescence detection without having to inject the light directly on or in the immediate neighborhood of the defect.

It has been found that by injecting light at the occlusal, facial or lingual surface such that the path of at least some of the photons between the point of light injection and the mesial or distal proximal surface remains substantially in the enamel portion of the tooth, it is possible to detect a light signal characteristic of the dental defect in the proximal surface. Without wishing to be bound by theory, the reflection/refraction or luminescence signal can be detected when the path of the light substantially avoids the dentin.

Light that is injected in the tooth will be reflected/refracted by tooth structures including at the site of the defect or it can excite natural molecules resulting in the generation of luminescence (fluorescence or phosphorescence) if a proper wavelength is used. The detected light from the reflection/refraction or luminescence provides a signal indicative of the presence or absence of the defect on the proximal surface (interproximal area).

Figure 3A:
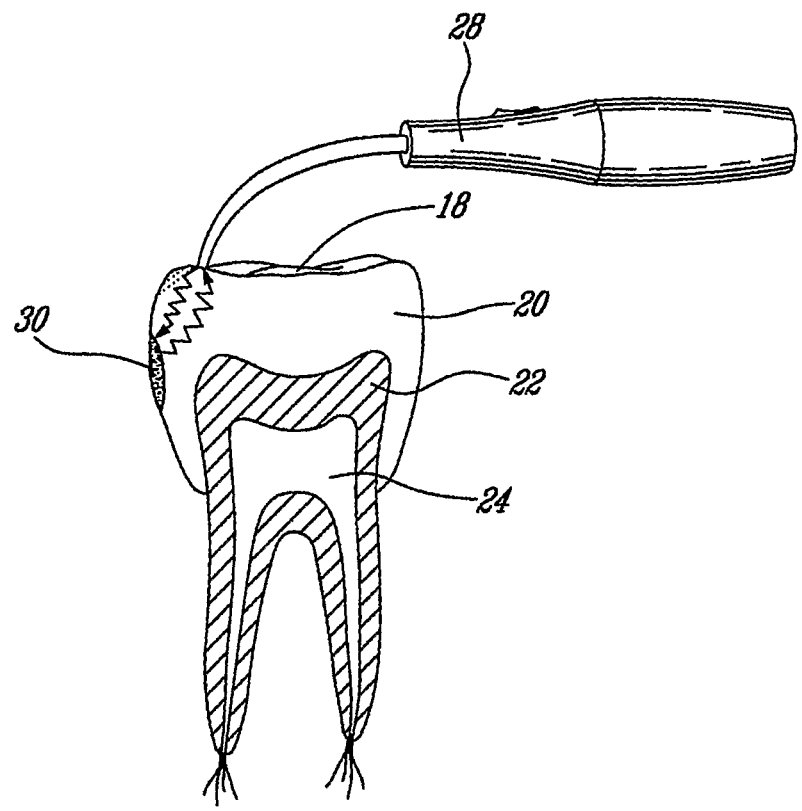
FIG. 3A is a schematic representation of the path of light within the tooth when probed according to an embodiment of the invention.
Figure 3B:
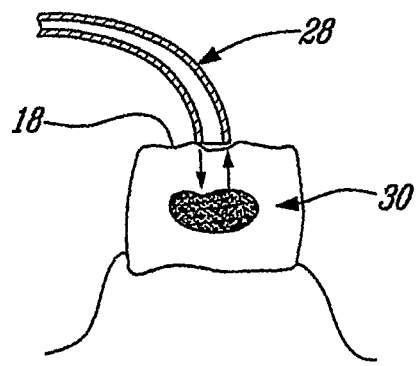
FIG. 3B is an interproximal view of FIG. 3A.
Figure 3C:
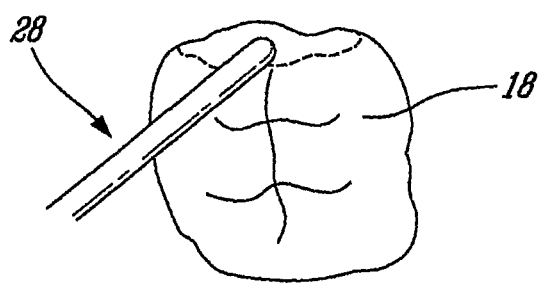
FIG. 3C is an occlusal view of FIG. 3A.

In one embodiment of the invention light is injected with a light probe 28 at the mesial or distal edge of the occlusal surface of a tooth as shown in FIG. 3A and the light reaches the defect 30 (such as a carie) in the interproximal region and is reflected/diffracted, or a luminescence signal is generated, and the signal is detected. Interproximal and occlusal view of FIG. 3A are shown in FIGS. 3B and 3C.

When operating in the reflection//refraction mode, the point of light injection and the point of light detection can be the same. However in a preferred embodiment they are spaced apart so as to avoid interference between the injected and the detected light. Optimal spatial separation between injection and detection point will depend on factors such as the intensity of the light, structure of the tooth, configuration of the light source and detector of the probe and the like. In a preferred embodiment the separation is between 0 µm and 10 mm. In a more preferred embodiment the separation is between 150 µm and 5 mm.

When operating in the luminescence mode the point of injection and the point of detection can be the same since injection and detection are effected at different wavelengths, i.e. at different excitation and emission wavelengths. Thus the probe can be equipped with appropriate optical filters so as to only allow light at the excitation wavelength to reach the detector. It will be appreciated however that the injection and detection points may also be separated as in the case of the reflection/refraction mode. in such a case a filter at the detector may still be required to filter out reflected/refracted light.

It is also possible to inject the light at an injection point that is on a different surface than the detection. Thus it is also possible to inject the light at a point on one surface, say the facial surface near the proximal surface, and detect the reflection (or fluorescence) at a different surface, say the lingual or occlusal surface. This approach is to be distinguished from the trans-illumination approach in which light absorption is measured as opposed to reflection/refraction or luminescence. The magnitude of the signal detected using a given light intensity and wavelength will depend on the actual localization of the injection and detection points relative to the defect in the interproximal area as well as on the size of the defect. It may accordingly be possible to get an approximation of the size and position of the defect by acquiring signals at different injection/detection points configurations.

The position of the injection and detection point to be used for detecting interproximal tooth defects may be determined by identifying the regions at which reflection/refraction (or luminescence) from dentin is detected and using this "map" to avoid positions at which the dentin signal interferes with the signal from the interproximal region.

It has been found that the intensity of the reflection/refraction of the light at given wavelengths or ranges of wavelengths is different for teeth that exhibit defects in the interproximal region than for healthy teeth in the same region. In one embodiment the intensity of the reflection/refraction at one wavelength ($I_{\lambda 1}$) can be plotted against the intensity at a second wavelength ($I_{\lambda 2}$) (see for example FIGS. 4A and 4B). Standard (reference) plots can be generated by acquiring multiple readings at the two wavelengths ($I_{\lambda 1}$, $I_{\lambda 2}$) from teeth exhibiting a healthy interproximal region and teeth exhibiting a defect such as carie. The reference plots exhibit areas in which the coordinates ($I_{\lambda 1}$, $I_{\lambda 2}$) are characteristic of diseased or normal teeth. Actual measurements for diagnosis purposes can be compared to the standard plots.

Figure 4A:
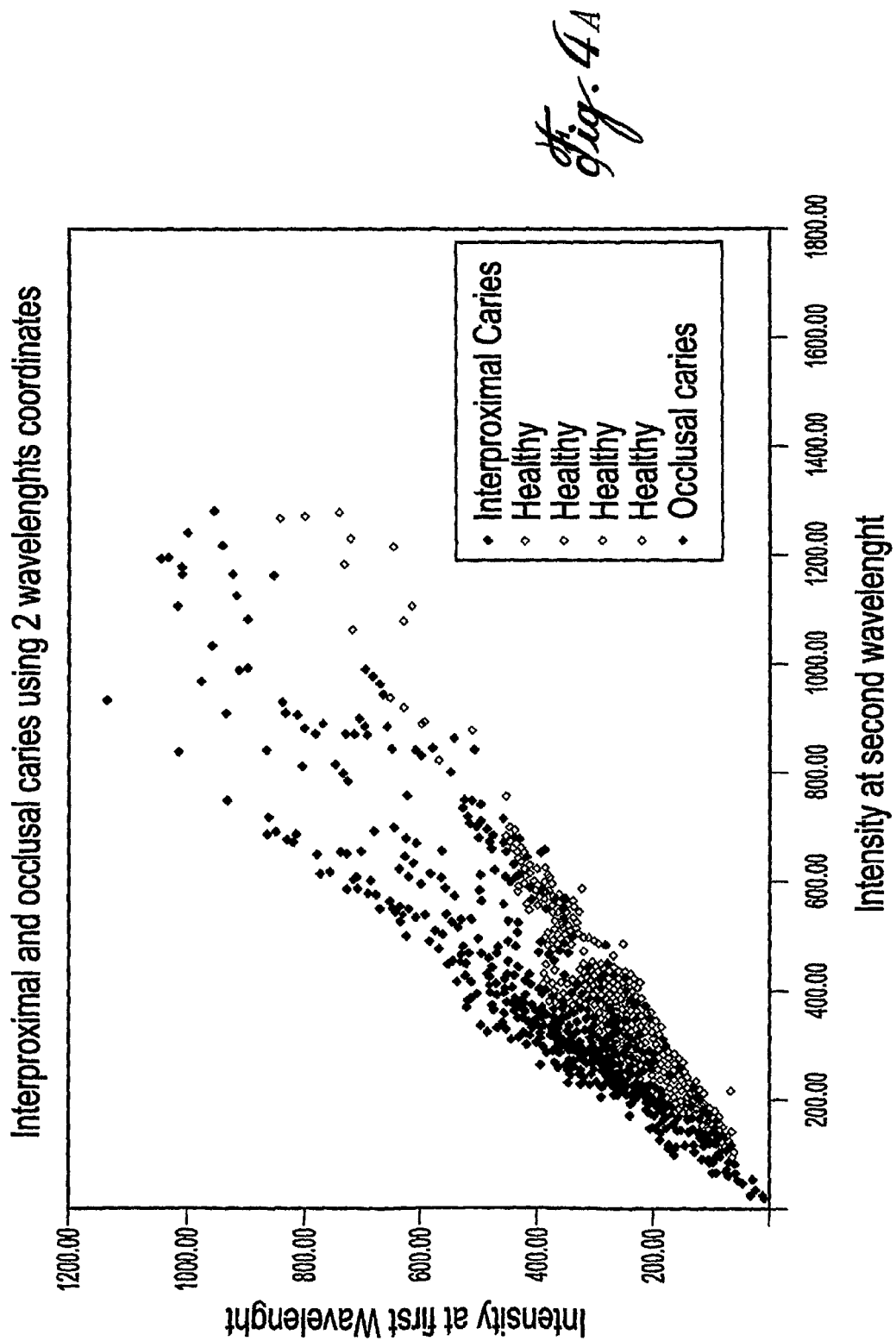
FIG. 4A is a graphic of the intensity of reflected/refracted light at one wavelength vs. intensity of reflected/refracted light at a different wavelength for healthy teeth (white symbols) and teeth exhibiting occlusal (gray symbols) or interproximal (black symbols) caries.
Figure 4B:
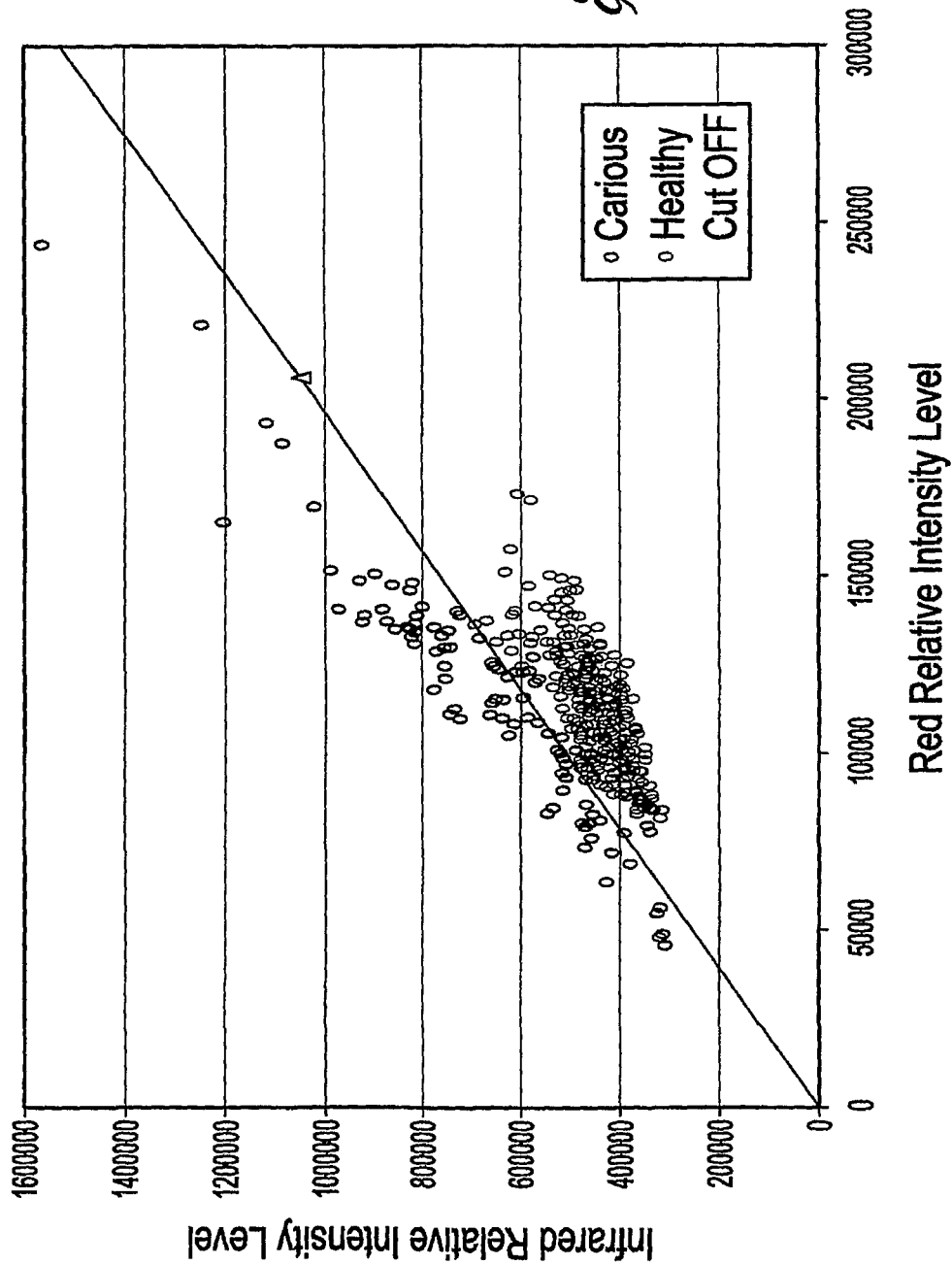
FIG. 4B is a graphic of the intensity of reflected/refracted light in the infrared region vs. the red region of the spectrum for extracted teeth that have been inspected via the occlusal region, the symbols above the line represents carious teeth in the interproximal region and the symbols below the line are from healthy tooth.

As can be seen in FIG. 4 defects such as caries in different areas of a tooth can be distinguished by establishing the relationship between intensity measurements at two or more wavelengths. From the particular example in FIG. 4A, in which intensity measurements for healthy teeth and teeth exhibiting interproximal or occlusal caries are plotted at two wavelengths it can be seen that the Intensities are clustered in a specific region (or regions).

Plots of $I_{\lambda 1}$ vs $I_{\lambda 2}$ also advantageously take into accounts variations in the signal intensity that are the results of variations in the position of the injection point and/or detection point relative to the position of the defect on the tooth. Such plots also take into account the size and position of the defect insofar as it can affect the intensity of the signal.

It will be appreciated that more than two wavelengths can be used. The number of wavelengths used dictates the dimensionality of the graph. Thus, for example a three dimensional graph can be used to represent the correlation between the intensity at three wavelengths. Increasing the number of wavelengths at which measurements are obtained and thus the dimensionality of the graph increases the accuracy and specificity of the diagnosis. Without wishing to be bound by any theory, since the reflection/refraction is wavelength dependent, each wavelength can provide specific information about the nature of the defect.

When diagnosis measurements are obtained from a patient, the intensities of the reflection/refraction at two or more wavelengths (i.e. the coordinates ($I_{\lambda,1}$, $I_{\lambda,2}$)) are compared to the reference graph to determine whether there is presence of a carie or not in the interproximal area.

It will be appreciated that other approaches to analyze the detected light may also provide indication of the presence of defects. For example the measurements may be reported in terms of ratios of intensities at different wavelengths or even intensity at a single wavelength.

The range of wavelengths that can be used is preferably between 300 and 3000 nm. In the case of luminescence specific wavelengths may be more effective for the excitation of molecules. Optimal wavelengths may be determined by injecting light at different wavelength and detecting the emitted luminescence.

Injection and detection of light can be achieved using optical instruments that are known in the art such as described in US patent applications US20050181333, US20030143510 and US20040106081 or other such devices. These instruments can be adapted to comprise a processor capable of computing and comparing the intensities as described above to provide a signal to the user when a measurement indicates the presence of a defect in the interproximal region of a tooth.

Furthermore, polarized and/or coherent light may also be used as the light source to be injected according to the method of the present invention. Detection of such light for the purpose of detecting dental defects has been described. See for example Fried et al (Journal of Biomedical Optics; vol 7; No 4; 618-627, 2002).

While the invention has been described in connection with specific embodiments thereof, it will be understood that it is capable of further modifications and this application is intended to cover any variations, uses, or adaptations of the invention following, in general, the principles of the invention and including such departures from the present disclosures as come within known or customary practice within the art to which the invention pertains and as may be applied to the essential features herein before set forth, and as follows in the scope of the appended claims.

The invention claimed is:

1. A method for detection of an interproximal defect in a tooth, comprising:
    injecting incident light at one or more wavelengths at a mesial or distal region of an occlusal surface of said tooth, such that said incident light can reach said interproximal defect on an interproximal surface substantially through enamel structure;
    detecting at a detection site on said occlusal surface reflected light; and
    analyzing said reflected light to provide a signal indicating a presence of said interproximal defect wherein said analyzing comprises obtaining an intensity of said detected light and comparing said intensity with reference intensities obtained from healthy interproximal tooth regions and interproximal tooth regions exhibiting defects wherein light reflected from said regions exhibiting defect is greater than said healthy interproximal tooth regions.

2. The method as claimed in claim 1 wherein said defect is caries.

3. The method as claimed in claim 1 wherein an injection site and said detection site are separated by a distance of between about 0 and 10 mm.

4. The method as claimed in claim 1 wherein an injection site and said detection site are separated by a distance of between about 150 mm and 5 mm.

5. The method as claimed in claim 1 further comprising selecting an injection and said detection site based on a contribution to light reflected from dentin such that said incident light can reach said interproximal defect substantially through enamel structure.

6. The method as claimed in claim 1 wherein a ratio of intensities at two or more wavelengths is obtained.

7. The method as claimed in claim 1 wherein said intensity is detected at two or more wavelengths to provide intensity coordinates in two or more dimensional space, and wherein said coordinates are compared to reference coordinates of healthy tooth regions and tooth regions exhibiting defects.

8. The method as claimed in claim 1 wherein said one or more wavelengths of the incident light are in the range of 300 to 3000 nm.

9. The method as claimed in claim 1 wherein said incident light is coherent and/or polarized light.

10. The method as claimed in claim 1 wherein said defect is selected from the group consisting of, tartar, plaque, dental concretion, fracture and presence of blood.

* * * * *